US011583227B2

United States Patent
Sarussi et al.

(10) Patent No.: US 11,583,227 B2
(45) Date of Patent: Feb. 21, 2023

(54) WEARABLE APPARATUS AND METHOD FOR MONITORING MEDICAL PROPERTIES

(71) Applicant: BIOBEAT TECHNOLOGIES LTD., Petach Tikva (IL)

(72) Inventors: Israel Sarussi, Ganei Tal (IL); Johanan May, Petach Tikva (IL); Arik Ben Ishay, Zoran (IL); Refael Gil Koby, Kochav Yair (IL)

(73) Assignee: BIOBEAT TECHNOLOGIES LTD., Petach Tikva (IL)

( * ) Notice: Subject to any disclaimer, the term of this patent is extended or adjusted under 35 U.S.C. 154(b) by 0 days.

(21) Appl. No.: 17/327,799

(22) Filed: May 24, 2021

(65) Prior Publication Data
US 2021/0275095 A1    Sep. 9, 2021

Related U.S. Application Data

(63) Continuation of application No. 17/292,472, filed as application No. PCT/IL2019/051204 on Nov. 4, 2019.

(60) Provisional application No. 62/758,642, filed on Nov. 11, 2018.

(51) Int. Cl.
| | |
|---|---|
| *A61B 5/00* | (2006.01) |
| *A61B 5/0531* | (2021.01) |
| *A61B 5/263* | (2021.01) |
| *A61B 5/339* | (2021.01) |
| *A61B 5/333* | (2021.01) |
| *A61B 5/318* | (2021.01) |

(52) U.S. Cl.
CPC .......... *A61B 5/6801* (2013.01); *A61B 5/0531* (2013.01); *A61B 5/263* (2021.01); *A61B 5/333* (2021.01); *A61B 5/339* (2021.01); *A61B 5/318* (2021.01); *A61B 2503/40* (2013.01); *A61B 2560/0443* (2013.01); *A61B 2562/227* (2013.01)

(58) Field of Classification Search
CPC ............................ A61B 5/6801; A61B 5/0531
See application file for complete search history.

(56) References Cited

U.S. PATENT DOCUMENTS

| | | | |
|---|---|---|---|
| 3,973,129 | A | 8/1976 | Blumberg et al. |
| 4,703,758 | A | 11/1987 | Omura et al. |
| 5,273,036 | A | 12/1993 | Kronberg et al. |

(Continued)

FOREIGN PATENT DOCUMENTS

| | | |
|---|---|---|
| CN | 104000572 | 8/2014 |
| CN | 203885491 | 10/2014 |

(Continued)

OTHER PUBLICATIONS

An Office Action dated Apr. 1, 2019, which issued during the prosecution of U.S. Appl. No. 15/218,123.

(Continued)

*Primary Examiner* — Alex M Valvis
*Assistant Examiner* — Yasmeen S Warsi
(74) *Attorney, Agent, or Firm* — Sughrue Mion, PLLC

(57) ABSTRACT

A wearable device for monitoring medical properties of a patient, the device having a rigid frame, multiple members coupled to the rigid frame, and a housing having an electrical circuit, where the housing is secured to the rigid frame, where the rigid frame surrounds a void, and where the void is configured to accommodate a bottom surface of the housing.

10 Claims, 8 Drawing Sheets

(56) References Cited

U.S. PATENT DOCUMENTS

| | | | |
|---|---|---|---|
| 5,377,673 A | 1/1995 | Van Dell et al. |
| 5,396,893 A | 3/1995 | Oberg et al. |
| 5,687,721 A | 11/1997 | Kuhls et al. |
| 5,800,348 A | 9/1998 | Kaestle |
| 5,868,671 A | 2/1999 | Mahoney |
| 6,027,452 A | 2/2000 | Flaherty et al. |
| 6,134,458 A | 10/2000 | Rosenthal |
| 6,252,032 B1 | 6/2001 | Van Antwerp et al. |
| 6,434,420 B1 | 8/2002 | Taheri |
| 6,491,647 B1 | 12/2002 | Bridger et al. |
| 6,493,567 B1 | 12/2002 | Krivitski et al. |
| 6,553,242 B1 | 4/2003 | Sarussi |
| 6,556,851 B1 | 4/2003 | Ott et al. |
| 6,616,613 B1 | 9/2003 | Goodman et al. |
| 6,714,812 B1 | 3/2004 | Karjalainen et al. |
| 6,719,705 B2 | 4/2004 | Mills |
| 7,006,855 B1 | 2/2006 | Sarussi |
| 7,314,451 B2 | 1/2008 | Halperin et al. |
| 7,359,741 B2 | 4/2008 | Sarussi |
| 7,515,948 B1 | 4/2009 | Balberg et al. |
| 7,641,614 B2 | 1/2010 | Asada et al. |
| 7,650,176 B2 | 1/2010 | Sarussi et al. |
| 7,909,768 B1 | 3/2011 | Turcott |
| 7,953,474 B2 | 5/2011 | Hwang et al. |
| 8,055,321 B2 | 11/2011 | Bernreuter |
| 8,585,607 B2 | 11/2013 | Klap et al. |
| 8,725,226 B2 | 5/2014 | Isaacson |
| 8,821,418 B2 | 9/2014 | Meger et al. |
| 9,314,197 B2 | 4/2016 | Eisen et al. |
| 9,351,671 B2 | 5/2016 | Ruchti et al. |
| 9,449,493 B2 | 9/2016 | Shinar et al. |
| 9,642,537 B2 | 5/2017 | Felix et al. |
| 9,750,429 B1 | 9/2017 | Sackner et al. |
| 9,770,213 B2 | 9/2017 | Kirenko et al. |
| 9,883,809 B2 | 2/2018 | Klap et al. |
| 10,292,625 B2 | 5/2019 | Shinar et al. |
| 10,368,772 B2 | 8/2019 | Banet et al. |
| 10,786,211 B2 | 9/2020 | Halperin et al. |
| 10,806,351 B2 | 10/2020 | Moon et al. |
| 10,813,578 B1 | 10/2020 | Ben Ishay et al. |
| 10,856,752 B2 | 12/2020 | Banet et al. |
| 2002/0044279 A1 | 4/2002 | Khoury et al. |
| 2002/0099277 A1 | 7/2002 | Harry et al. |
| 2003/0149349 A1 | 8/2003 | Jensen |
| 2003/0220549 A1 | 11/2003 | Liu et al. |
| 2003/0233036 A1 | 12/2003 | Ansari et al. |
| 2004/0030258 A1 | 2/2004 | Williams et al. |
| 2004/0092822 A1 | 5/2004 | Robinson et al. |
| 2004/0111035 A1 | 6/2004 | Kondoh et al. |
| 2004/0158240 A1 | 8/2004 | Avrahami |
| 2004/0183997 A1 | 9/2004 | Suzuki |
| 2005/0002031 A1 | 1/2005 | Kraemer et al. |
| 2005/0075549 A1 | 4/2005 | Kondoh et al. |
| 2005/0096513 A1 | 5/2005 | Ozguz et al. |
| 2005/0113661 A1 | 5/2005 | Nazeri et al. |
| 2006/0079789 A1 | 4/2006 | Lee et al. |
| 2006/0094941 A1 | 5/2006 | Cho et al. |
| 2006/0151709 A1 | 7/2006 | Hahl |
| 2007/0000374 A1 | 1/2007 | Clark et al. |
| 2007/0038050 A1 | 2/2007 | Sarussi |
| 2007/0118054 A1 | 5/2007 | Pinhas et al. |
| 2007/0213607 A1 | 9/2007 | Mandelis et al. |
| 2008/0114260 A1 | 5/2008 | Lange et al. |
| 2008/0139953 A1 | 6/2008 | Baker et al. |
| 2008/0288026 A1 | 11/2008 | Cross et al. |
| 2009/0018421 A1 | 1/2009 | Sarussi et al. |
| 2009/0116017 A1 | 5/2009 | Xu et al. |
| 2010/0036265 A1 | 2/2010 | Kim et al. |
| 2010/0056887 A1 | 3/2010 | Kimura et al. |
| 2010/0081913 A1 | 4/2010 | Cross et al. |
| 2010/0105996 A1 | 4/2010 | Segman |
| 2010/0130840 A1 | 5/2010 | Isaacson |
| 2010/0137779 A1 | 6/2010 | Seitz |
| 2010/0256518 A1 | 10/2010 | Yu et al. |
| 2010/0276733 A1 | 11/2010 | Li |
| 2011/0152694 A1 | 6/2011 | Shimoyama et al. |
| 2012/0009126 A1 | 1/2012 | Singaram et al. |
| 2012/0132211 A1 | 5/2012 | Halperin et al. |
| 2012/0143067 A1 | 6/2012 | Watson et al. |
| 2012/0253142 A1 | 10/2012 | Meger et al. |
| 2012/0283535 A1 | 11/2012 | Sarussi |
| 2013/0137998 A1 | 5/2013 | Lange et al. |
| 2013/0267791 A1 | 10/2013 | Halperin et al. |
| 2013/0281866 A1 | 10/2013 | Shinar et al. |
| 2013/0296674 A1 | 11/2013 | Watson et al. |
| 2013/0324860 A1 | 12/2013 | Borgos et al. |
| 2014/0051946 A1 | 2/2014 | Arne et al. |
| 2014/0058272 A1 | 2/2014 | Naing et al. |
| 2014/0275852 A1 | 9/2014 | Hong et al. |
| 2015/0036133 A1 | 2/2015 | Uematsu et al. |
| 2015/0087932 A1 | 3/2015 | Halperin et al. |
| 2015/0094552 A1 | 4/2015 | Golda et al. |
| 2015/0276589 A1 | 10/2015 | Wagner et al. |
| 2015/0327792 A1 | 11/2015 | Shinar et al. |
| 2015/0351690 A1 | 12/2015 | Toth et al. |
| 2015/0366469 A1 | 12/2015 | Harris et al. |
| 2015/0374255 A1 | 12/2015 | Vasapollo |
| 2016/0058428 A1 | 3/2016 | Shinar et al. |
| 2016/0061726 A1 | 3/2016 | Ness et al. |
| 2016/0183818 A1 | 6/2016 | Richards et al. |
| 2016/0192868 A1 | 7/2016 | Levant et al. |
| 2016/0192884 A1 | 7/2016 | Levant et al. |
| 2017/0014056 A1 | 1/2017 | Newberry |
| 2017/0020399 A1 | 1/2017 | Shemesh et al. |
| 2017/0055855 A1 | 3/2017 | Yoon |
| 2017/0164848 A1 | 6/2017 | Nadeau et al. |
| 2017/0188872 A1* | 7/2017 | Hughes ............... A61B 5/361 |
| 2017/0238819 A1 | 8/2017 | Waller et al. |
| 2017/0281017 A1 | 10/2017 | Halperin et al. |
| 2017/0292908 A1 | 10/2017 | Wilk et al. |
| 2017/0305132 A1 | 10/2017 | Dollase et al. |
| 2018/0000362 A1 | 1/2018 | Matsuo et al. |
| 2018/0020960 A1 | 1/2018 | Sarussi et al. |
| 2018/0042496 A1 | 2/2018 | Lachhman et al. |
| 2018/0146870 A1 | 5/2018 | Shemesh et al. |
| 2018/0146877 A1 | 5/2018 | Baker et al. |
| 2018/0303353 A1 | 10/2018 | Baxi et al. |
| 2018/0317852 A1 | 11/2018 | MacDonald et al. |
| 2019/0083044 A1 | 3/2019 | Halperin et al. |
| 2019/0090860 A1 | 3/2019 | Shinar et al. |
| 2020/0214579 A1 | 7/2020 | Phillips et al. |
| 2020/0281523 A1 | 9/2020 | Maidel et al. |
| 2020/0367760 A1 | 11/2020 | Klaassen et al. |
| 2021/0100489 A1 | 4/2021 | Katz et al. |
| 2021/0386308 A1 | 12/2021 | Ben Ishay et al. |
| 2022/0015681 A1 | 1/2022 | Sarussi et al. |

FOREIGN PATENT DOCUMENTS

| | | |
|---|---|---|
| CN | 104605835 | 5/2015 |
| CN | 105943005 | 9/2016 |
| CN | 206558105 | 10/2017 |
| CN | 107411702 | 12/2017 |
| DE | 4446390 | 7/1996 |
| DE | 102011101934 | 11/2012 |
| EP | 0144509 | 6/1985 |
| EP | 0443267 | 8/1991 |
| EP | 1520514 | 4/2005 |
| EP | 1139865 | 10/2007 |
| EP | 1936356 | 6/2008 |
| EP | 2270516 | 1/2011 |
| EP | 3033992 | 6/2016 |
| FR | 2105327 | 4/1972 |
| GB | 2357846 | 7/2001 |
| JP | 2004113434 | 4/2004 |
| JP | 2009168670 | 7/2009 |
| JP | 2013068461 | 4/2013 |
| JP | 2014117503 | 6/2014 |
| JP | 2014130046 | 7/2014 |
| KR | 100756654 | 9/2007 |
| KR | 20080044223 | 8/2008 |
| KR | 20130065513 | 6/2013 |
| KR | 20170064906 | 6/2017 |
| WO | 89/11825 | 12/1989 |

(56) References Cited

FOREIGN PATENT DOCUMENTS

| WO | 92/07511 | 5/1992 |
|---|---|---|
| WO | 96/39922 | 12/1996 |
| WO | 99/63883 | 12/1999 |
| WO | 00/22982 | 4/2000 |
| WO | 00/43536 | 7/2000 |
| WO | 00/60350 | 10/2000 |
| WO | 01/17421 | 3/2001 |
| WO | 01/43624 | 6/2001 |
| WO | 01/53806 | 7/2001 |
| WO | 01/60248 | 8/2001 |
| WO | 01/94938 | 12/2001 |
| WO | 03/025562 | 3/2003 |
| WO | 03/096876 | 11/2003 |
| WO | 2004/090786 | 10/2004 |
| WO | 2009/047774 | 4/2009 |
| WO | 2016/115369 | 7/2016 |
| WO | 2016/168090 | 10/2016 |
| WO | 2016/178119 | 11/2016 |
| WO | 2017/004129 | 1/2017 |
| WO | 2017/115343 | 7/2017 |
| WO | 2018/013656 | 1/2018 |
| WO | 2018/020492 | 2/2018 |
| WO | 2018/069931 | 4/2018 |
| WO | 2018/202824 | 11/2018 |
| WO | 2019/172570 | 9/2019 |
| WO | 2020/095296 | 5/2020 |
| WO | 2021/130749 | 7/2021 |

OTHER PUBLICATIONS

An Office Action dated Sep. 11, 2018, which issued during the prosecution of U.S. Appl. No. 15/218,123.
Tones Filho, Ivo P., James Terner, and Linda Scheider. "Resonance Raman spectroscopy of human sickle cell hemoglobin from transgenic mice." The FASEB Journal 23 (2009): 768-2.—Abstract.
Hayes, Matthew J., and Peter R. Smith. "Artifact reduction in photoplethysmography." Applied Optics 37.31 (1998): 7437-7446.
Wauschkuhn, Constantin A., et al. "Circadian periodicity of cerebral blood flow revealed by laser-Doppler flowmetry in awake rats: relation to blood pressure and activity." American Journal of Physiology—Heart and Circulatory Physiology 289.4 (2005): H1662-H1668.
Draghici, Adina E., et al. "Functional Near Infrared Spectroscopy for Measuring Bone Hemoglobin Content after Exercise in Individuals with Spinal Cord Injury."—Conference Abstract.
Byrom, Bill, et al. "A review evaluating the validity of smartphone sensors and components to measure clinical outcomes in clinical research." Value in Health 19.3 (2016): A72.
Zirk, K., H. Pötzschke, and W. K. R. Barnikol. "Ein miniaturisierbares, sehr empfindliches Polarimeter als Detektor einer implantierbaren Glukosesonde. II. Opto-elektronische Verstärkung und Verarbeitung der Meßsignale—A Miniaturisable Highly Sensitive Polarimeter for Use as a Detector in an Implantable Glucose Probe. II. Optoelectronic Amplification and Processing of Measuring Signals." (2001): 262-272.—Full article in German and English Abstract.
Abay, T. Y., and P. A. Kyriacou. "Comparison of NIRS, laser doppler flowmetry, photoplethysmography, and pulse oximetry during vascular occlusion challenges." Physiological Measurement 37.4 (2016): 503.—ABstract.
Sakota, Daisuke, and Setsuo Takatani. "Plasma surface reflectance spectroscopy for non-invasive and continuous monitoring of extracellular component of blood." Optical Sensing and Detection II. vol. 8439. SPIE, 2012.—Abstract.
U.S. Appl. No. 62/758,642, filed Nov. 11, 2018.
An Office Action together with an English Summary dated Feb. 25, 2022 which issued during the prosecution of Chinese Patent Application No. 201780057511.9.
An Office Action dated Mar. 6, 2020, which issued during the prosecution of U.S. Appl. No. 16/726,976.
Wolf, Martin, et al. "Detection of the fast neuronal signal on the motor cortex using functional frequency domain near infrared spectroscopy." Oxygen Transport to Tissue XXIII. Springer, Boston, MA, 2003. 193-197.—Abstract.
An International Search Report and a Written Opinion both dated Oct. 22, 2017, which issued during the prosecution of Applicant's PCT/IL2017/050752.
Mozaffarieh, Maneli, et al. "Relationship between optic nerve head and finger blood flow." European journal of ophthalmology 20.1 (2010): 136-141.—Abstract.
Nogawa, Masamichi, et al. "New hybrid reflectance optical pulse oximetry sensor for lower oxygen saturation measurement and for broader clinical application." Biomedical Sensing, Imaging, and Tracking Technologies II. vol. 2976. SPIE, 1997.
Petrig, B. L., and L. Follonier. "New ray tracing model for the estimation of power spectral properties in laser Doppler velocimetry of retinal vessels." Investigative Ophthalmology & Visual Science 46.13 (2005): 4290-4290.—Abstract.
An International Search Report and a Written Opinion both dated Feb. 16, 2020, which issued during the prosecution of Applicant's PCT/IL2019/051204.
European Search Report dated Dec. 11, 2019 which issued during the prosecution of Applicant's European App No. 17833695.4.
An International Search Report and a Written Opinion both dated Mar. 25, 2021, which issued during the prosecution of Applicant's PCT/IL2020/051314.
Villanueva, Rachel, et al. "Effect of peripheral perfusion on accuracy of pulse oximetry in children." Journal of clinical anesthesia 11.4 (1999): 317-322.—Abstract.
An Office Action dated Jul. 19, 2022, which issued during the prosecution of U.S. Appl. No. 16/898,461.
European Search Report dated Jul. 21, 2022 which issued during the prosecution of Applicant's European App No. 19881827.0.
An International Search Report and a Written Opinion both dated Aug. 31, 2022, which issued during the prosecution of Applicant's PCT/IL2022/050531.
Larsen, Vagn H., Theis Hansen, and Steen L. Nielsen. "Oxygen status determined by the photo-electric method-a circular fingerprobe constructed for detection of blood oxygen content, blood flow and vascular density." Scandinavian Journal of Clinical and Laboratory Investigation 53.sup214 (1993): 75-81.
Maattala, Miia, et al. "Optimum place for measuring pulse oximeter signal in wireless sensor-belt or wrist-band." 2007 International Conference on Convergence Information Technology (ICCIT 2007). IEEE, 2007.
Vacas-Jacques, Paulino, et al. "Development and validation of a physiological tag for monitoring oxygen saturation in muscle of free-diving whales." Lasers in Surgery and Medicine. vol. 44. Commerce Place, 350 Main St, Malden 02148, MA USA: Wiley-Blackwell, 2012.—Abstract.
Lu, Xiuling, et al. "Disuccinimidyl suberate cross-linked hemoglobin as a novel red blood cell substitute." Science in China. Series C, Life Sciences 48.1 (2005): 49-60.—Abstract.
Myllylä, Teemu S., et al. "Fibre optic sensor for non-invasive monitoring of blood pressure during MRI scanning." Journal of biophotonics 4.1-2 (2011): 98-107.—Abstract.
Physics and Technology of Emitters and Detectors, Vishay Telefunken, Dec. 1999, p. 11-24.
Harja, Juha, Teemu S. Myllylä, and Risto A. Myllylä. "MRI-compatible noninvasive continuous blood pressure measurement using fiber optics." Saratov Fall Meeting 2009: International School for Junior Scientists and Students on Optics, Laser Physics, and Biophotonics. vol. 7547. SPIE, 2010.—Abstract.
Lee, Hwansung, and Yoshiyuki Taenaka. "Hydrodynamic characteristics of the Edwards MIRA bileaflet valve in a pneumatic ventricular assist device." ASAIO Journal 53.4 (2007): 397-402.
Adam, N., and P. Ghosh. "Hyaluronan molecular weight and polydispersity in some commercial intra-articular injectable preparations and in synovial fluid." Inflammation Research 50.6 (2001): 294-299.—Abstract.
An Office Action together issued during the prosecution with an English Summary dated Aug. 17, 2021 which of Chinese Patent Application No. 201780057511.9.

(56) References Cited

OTHER PUBLICATIONS

An Office Action together with an English Summary dated Jan. 22, 2021 which issued during the prosecution of Chinese Patent Application No. 201780057511.9.

Download of scientific diagram from researchgate.com—downloaded on Jun. 10, 2022.

Nie, Baoqing, et al. "Droplet-based interfacial capacitive sensing." Lab on a Chip 12.6 (2012): 1110-1118.—Abstract.

An International Search Report and a Written Opinion both dated Jul. 25, 2021, which issued during the prosecution of Applicant's PCT/IL2021/050711.

* cited by examiner

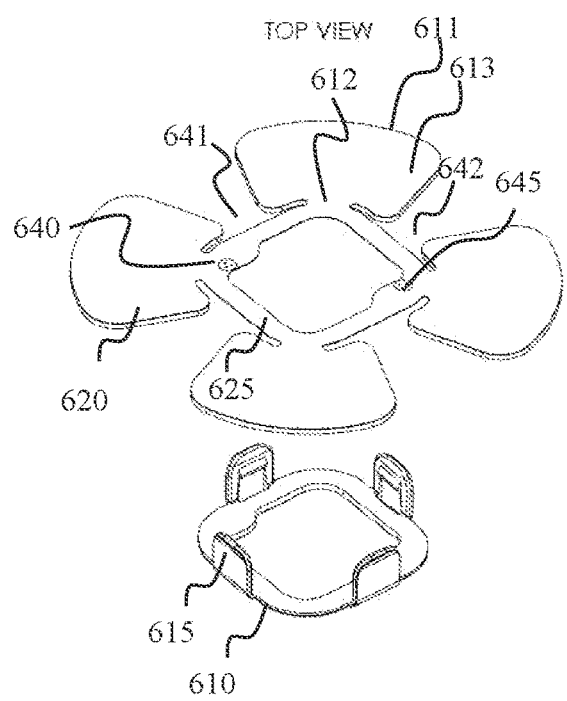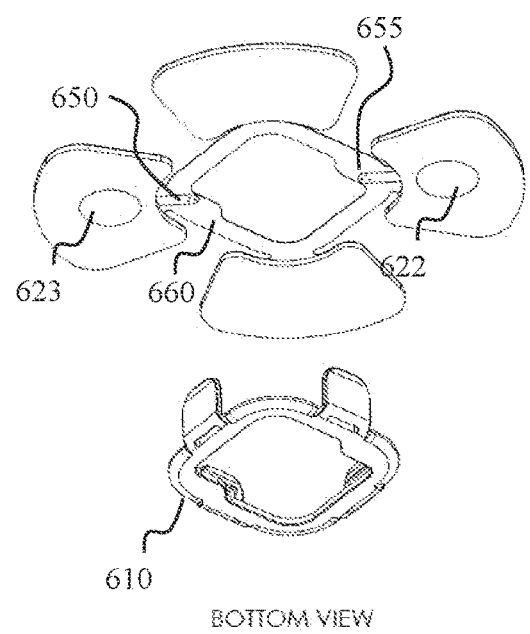
FIG. 6A
FIG. 6B

| | |
|---|---|
| 810 | OBTAINING A SENSOR MODULE AND AN ELECTRICAL CIRCUIT EMBODIED IN A HOUSING AND A CONNECTING MEMBER |
| 820 | SECURING THE CONNECTING MEMBER AT A BOTTOM SIDE OF THE SENSOR MODULE, THUS SECURING THE CONDUCTIVE ELEMENTS TO THE RIGID FRAME |
| 830 | MOUNTING THE HOUSING FROM THE TOP SECTION OF THE SENSOR MODULE, SECURED BY THE HOLDERS OF THE CONNECTING MEMBER |
| 840 | VERIFYING ELECTRICAL COUPLING BETWEEN THE CONDUCTIVITY MEMBERS AND THE ELECTRICAL CIRCUIT INSIDE THE HOUSING |

FIG. 8

WEARABLE APPARATUS AND METHOD FOR MONITORING MEDICAL PROPERTIES

FIELD OF THE INVENTION

The present disclosure generally relates to wearable devices, and more particularly relates to wearable devices for monitoring medical properties of patients.

BACKGROUND OF THE INVENTION

An electrocardiogram (ECG) is a tool used by physicians to diagnose heart problems and other potential health concerns. Diagnostic efficacy of problems, like syncope or cardiac arrhythmias, can be improved through the use of long-term extended wear ECG monitoring. Recording sufficient ECG and related physiological data over an extended period of time remains a significant challenge to healthcare providers, despite over a 40-year history of such efforts. Extended period monitoring essentially enables a physician to identify cardiac conditions, specifically, rhythm disorders, and other physiological events of potential concern.

Conventionally, maintaining continual contact between ECG electrodes and the skin after a day or two has been a problem. Time, dirt, moisture, and other environmental contaminants, as well as perspiration, skin oil, and dead skin cells from the patient's body, can get between an ECG electrode and the skin's surface. All of these factors adversely affect the quality of physical signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless Thus, it is desired to periodically remove or replace ECG electrodes during a long term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

SUMMARY OF THE INVENTION

It is an object of the subject matter to disclose a wearable device for monitoring medical properties of a patient, comprising a body, comprising multiple light-weight disposable members, one or more electrodes located on a bottom surface of the multiple light-weight disposable members, wherein the one or more electrodes are configured to be in physical contact with a patient's skin and configured to collect electrical information from the patient's skin, an electrical circuit placed inside a housing, said housing is secured to an upper side of the multiple light-weight disposable members, said electrical circuit is configured to analyze the electrical information collected by the one or more electrodes, one or more conductive members, each conductive member of the one or more conductive members having a proximal side connected to the one or more electrodes and a distal side connected to the housing of the electrical circuit, and a connecting member coupled to lateral surface or top surface of the housing of the electrical circuit, configured to secure the electrical circuit to the body.

In some cases, the electrical information collected from the patient's skin comprises ECG-related information. In some cases, the electrical circuit is configured to process the electrical information. The wearable device of claim 1, further comprises a housing for storing the electrical circuit, wherein the electrical circuit is configured to display ECG-related information on a top surface of the housing based on the electrical information collected from the patient's skin.

In some cases, the bottom surface points towards the patient's skin when in use.

In some cases, the light-weight disposable members are made of a material selected from a group comprising fabric, paper, Low Density Polyethylene, Polyethylene terephthalate, Polyurethane, polyester, silicone, nonwoven fabric and a combination thereof.

The wearable device of claim 1, further comprising a two-side conductive passageway between the one or more electrodes located on the bottom surface of the light-weight disposable members and the electrical circuit is located upwards from the light-weight members.

In some cases, the light-weight disposable members are manufactured using a printing technology. In some cases, the connecting member is secured to the light-weight disposable members from a bottom section of the light-weight disposable members.

In some cases, the electrical circuit comprises a bottom section comprises a bottom surface and a secondary surface, said secondary surface forms a specific form in the bottom section, wherein the form is configured to sit inside a niche in the connecting member.

In some cases, the multiple light-weight disposable members are connected to a rigid frame that surrounds a void, wherein the void is configured to accommodate the bottom surface of the electrical circuit. In some cases, the multiple light-weight disposable members are foldable relative to the rigid frame using an elastic connector configured to physically secure the multiple light-weight disposable members to the rigid frame.

In some cases, the rigid frame comprises a frame bottom surface configured to be connected to the one or more conductive members that pass electrical information from the one or more electrodes and a frame top surface comprising one or more conductive areas configured to be secured to connectors connected to the housing of the electrical circuit.

In some cases, the electrical information passed from the first side of the one or more conductive areas to the second side using one or more apertures configured to contain a conductive fluid. In some cases, the conductive fluid comprises conductive ink.

In some cases, the one or more conductive members are connected to a bottom side of the one or more conductive areas, said bottom side of the one or more conductive areas comprises multiple apertures enabling passage of the conductive fluid as elaborated above.

In some cases, the housing of the electrical circuit comprises one or more connectors configured to be secured to the one or more conductive members that pass the electrical information from the one or more electrodes.

In some cases, the one or more connectors connect on one end to the housing of the electrical circuit and on another end to the one or more conductive members connected to the electrode.

In some cases, the connecting member secures the housing of the electrical circuit to the body only when electrical conductivity is enabled between the one or more connectors and the one or more conductive members. In some cases, the connecting member comprises a plurality of holders secured to a lateral surface or a top surface of the electrical circuit.

In some cases, the plurality of holders comprise an elastic section, wherein the elastic section is tensed when the plurality of holders move away from the connecting void.

In some cases, the light-weight disposable members comprise a distal side and a proximal side, said proximal side is narrower than the distal side, thereby forming lateral voids between the light-weight disposable members.

BRIEF DESCRIPTION OF THE DRAWINGS

The invention may be more clearly understood upon reading of the following detailed description of non-limiting exemplary embodiments thereof, with reference to the following drawings, in which:

FIGS. 6A-6B show a top view and a bottom view of the sensor module and the connecting module disassembled, according to exemplary embodiments of the subject matter;

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DETAILED DESCRIPTION OF THE INVENTION

Illustrative embodiments of the invention are described below. In the interest of clarity, not all features/components of an actual implementation are necessarily described.

The present invention discloses a wearable device for monitoring medical properties of a patient, either a person or animal. The wearable device comprises one or more electrodes configured to be secured and attached to the patient's skin and an electrical circuit connected to the one or more electrodes. The one or more electrodes are configured to collect electrical information from the patient's skin, for example ECG-related information such as blood pressure and the like. The one or more electrodes are an optional embodiment for the wearable device of the disclosed subject matter. The wearable device may comprise a camera or any other type of sensor configured to collect medical information from the patient's skin. The sensor may comprise a light emitter for emitting light towards the patient's skin and a collector for collecting the reflections from the patient's skin. The electrical information may include voltage, frequency, amplitude, conductivity and the like. The electrical information is passed to the electrical circuit via a conductive member connected to the one or more electrode. The electrical circuit may transmit the electrical information to a remote device. The electrical circuit may process the electrical information and display ECG-related information such as blood pressure, trends and the like.

The wearable device of the subject matter comprises a body having multiple light-weight disposable members. The one or more electrodes are physically attached to the multiple light-weight members. The multiple light-weight disposable members are configured to be secured to the patient's skin. The conductive member is attached to a bottom surface of the light-weight member and then connects to the electrical circuit, via a housing of the electrical circuit. This way, the electrical circuit is isolated from the patient's skin and the user's experience is improved.

Figure 1:
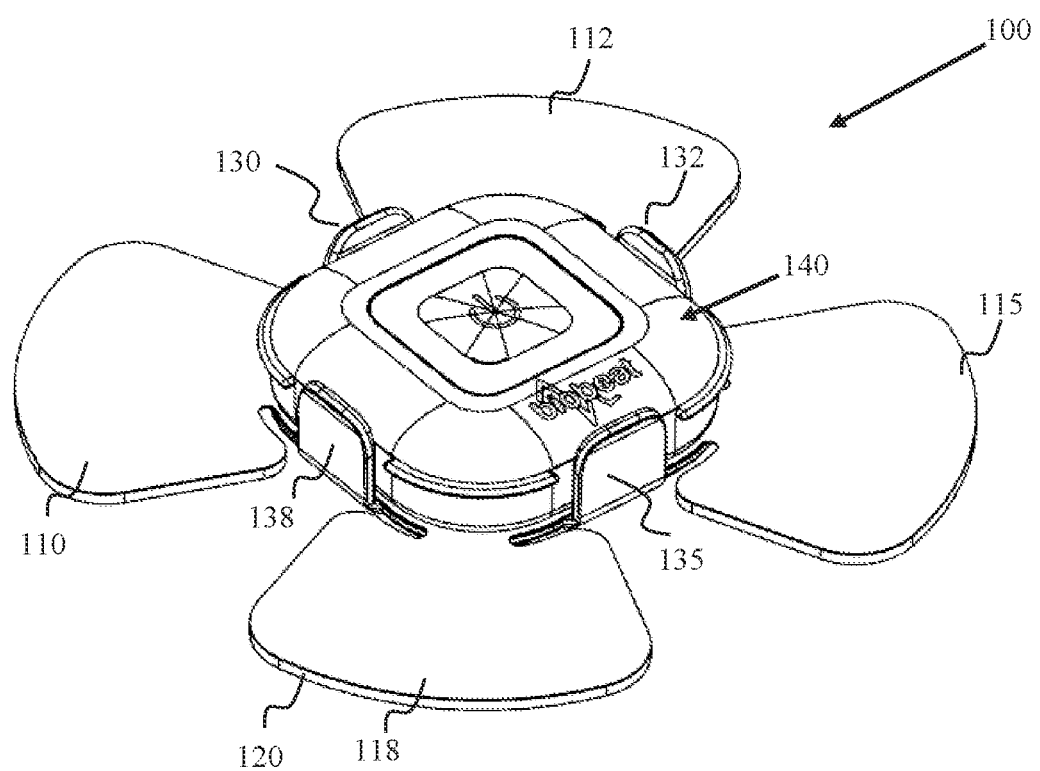
FIG. 1 discloses a top view of the wearable apparatus, according to exemplary embodiments of the subject matter.

FIG. 1 discloses a top view of the wearable apparatus, according to exemplary embodiments of the subject matter. The wearable apparatus 100 comprises electrical circuit 140 connected to a plurality of light-weight members 110, 112, 115 and 118. At least a portion of the plurality of light weight members 110, 112, 115 and 118 is attached to an electrode on the bottom surface, said bottom surface points towards the patient's skin when in use. The bottom surface may be defined as an opposite direction from the electrical circuit 140. The light-weight members 110, 112, 115 and 118 may be made of fabric, or another light weight material selected from a group comprising cotton, paper, LDPE foil (Low Density Polyethylene), PET (Polyethylene terephthalate) foil, PU (Polyurethane) foil, polyester, silicone, nonwoven fabric, and a combination thereof. The light weight members 110, 112, 115 and 118 may be multiple light-weight disposable members, while the electrical circuit is used multiple times. Defining the light-weight members 110, 112, 115 and 118 as disposable items requires the wearable device to enable a two-side conductive passageway between the one or more electrodes located on a bottom surface of the members and the electrical circuit 140 located upwards from the light-weight members 110, 112, 115 and 118. The two-side conductive passageway may also be defined as an electrical circuit board, such as a PCB, having circuitry in a both layers, a first layer facing the electrodes, and a second layer facing the electrical circuit 140. The conductive material, such as the conductive ink, moves electrical signals between the first layer and the second layer.

Defining the light-weight disposable members 110, 112, 115 and 118 as disposable items also encourages manufacturing the light-weight disposable members 110, 112, 115 and 118 using printing technology, to reduce manufacture costs. Such printing technology may be screen (silk) printing, hot stamping, laser printing, offset printing, pad (tampon) printing and the like. The conductive element is attached to the bottom surface of the electrical circuit 140, and is connected to the electrode, as elaborated below. In some other cases, the light-weight disposable members 110, 112, 115 and 118 may be manufactured using laser engraving, forming the conductive members in the middle of the light-weight disposable members 110, 112, 115 and 118. The light-weight disposable members 110, 112, 115 and 118 may also be manufactured using mechanical press.

In some exemplary cases, the wearable apparatus 100 comprises some light-weight members that are not secured to one or more electrodes. For example, light-weight members 110 and 115 are connected to one or more electrodes, while light-weight members 112 and 118 are not connected to electrodes and are part of the wearable apparatus 100 to improve grasping the apparatus 100 around the user's limb, for example the user's arm or leg.

The wearable apparatus 100 also comprises a connecting member configured to secure the electrical circuit 140 to the light-weight members 110, 112, 115 and 118, thus securing the electrical circuit 140 to the conductive element that transfers the electrical information from the electrodes. The connecting member comprises multiple holders 130, 132, 135 and 138 configured to secure the housing of the electrical circuit 140. The multiple holders 130, 132, 135 and 138 may be secured to a lateral surface of the electrical circuit 140 or to a top surface of the electrical circuit 140. In some exemplary cases, the connecting member is secured to the light-weight members 110, 112, 115 and 118 from the bottom section of the light-weight members 110, 112, 115 and 118, thus securing the housing of the electrical circuit 140 to the light-weight members 110, 112, 115 and 118. The multiple holders 130, 132, 135 and 138 may be made of a first holder member, which enables moving the holders away from the housing of the electrical circuit 140 when removing and securing the housing of the electrical circuit 140 on the connecting member. The first member may be located on the bottom side of the multiple holders 130, 132, 135 and 138, closer to the light-weight members 110, 112, 115 and 118. The multiple holders 130, 132, 135 and 138 may comprise a second member connected to the first member, said second member is more rigid and secures the electrical circuit 140 between the multiple holders 130, 132, 135 and 138.

Figure 2A:
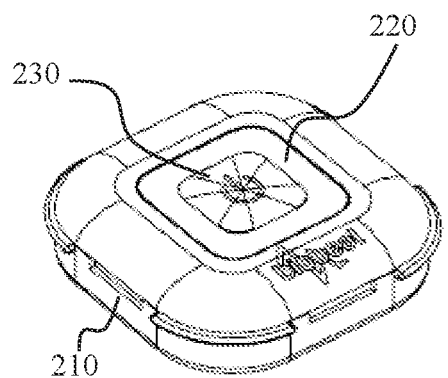
FIGS. 2A-2B show a top view and a bottom view of the electrical circuit, according to exemplary embodiments of the subject matter.
Figure 2B:
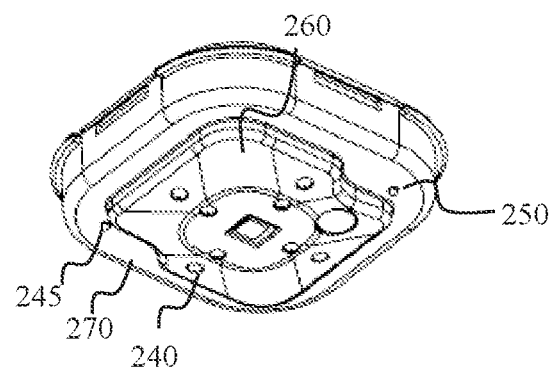

FIGS. 2A-2B show a top view and a bottom view of the electrical circuit, according to exemplary embodiments of the subject matter. The electrical circuit has a lateral surface 210, a top surface 220 and a bottom surface 260. The top surface 220 is accessible to the patient or medical professional, and may comprise an activation button 230, a display unit, a socket for connecting a cable to a display unit or another device and the like. The bottom section of the electrical circuit interfaces with the conductive element that transfers the electrical information from the electrodes. The bottom section comprises the bottom surface 260 and a secondary surface 270 that forms a specific form in the bottom surface. The form is configured to sit inside a niche in the connecting member, as elaborated below. The secondary surface 270 comprises one or more connectors 245, 250 configured to be secured to the conductive elements that pass the electrical information from the electrodes. The one or more connectors 245, 250 transfer the electrical information from the conductive elements into the electrical circuit located inside the housing. The one or more connectors 245, 250 may be pins, such as pogo pins, or a conductive surface, or a conductive spring leaves that connect on one end to the electrical circuit and on another end to the conductive members connected to the electrode. The one or more connectors 245, 250 are configured to be in physical contact with conductive areas 330, 332 of the top surface of the rigid frame 310 disclosed in FIG. 3. In some exemplary embodiments of the subject matter, the holders firmly secure the housing of the electrical circuit 140 to the body of the wearable device only when electrical conductivity is enabled between the one or more connectors 245, 250 and the conductive areas 330, 332 of the top surface of the rigid frame, said conductive areas are the output point of the conductive members that transfer electrical information from the one or more electrodes. The housing of the electrical circuit may be placed in a lower height, closer to the rigid frame, when the one or more connectors 245, 250 are in physical contact with the conductive areas 330, 332. The lower height of the housing of the electrical circuit enables firm secure of the holders.

The electrical circuit may comprise a memory unit configured to store a set of instructions, for example instructions configured to convert the electrical information collected by the electrodes into signals that represent medical information. The electrical circuit comprises a processing module configured to control the process of converting the electrical information into signals and may also perform more advanced processes, such as identifying trends in the collected medical information, identifying irregularities in the medical information and the like. The electrical circuit may be implemented as a printed circuit board or in any other manner in which electrical components are arranged in a predefined volume, as desired by a person skilled in the art.

Figure 3A:
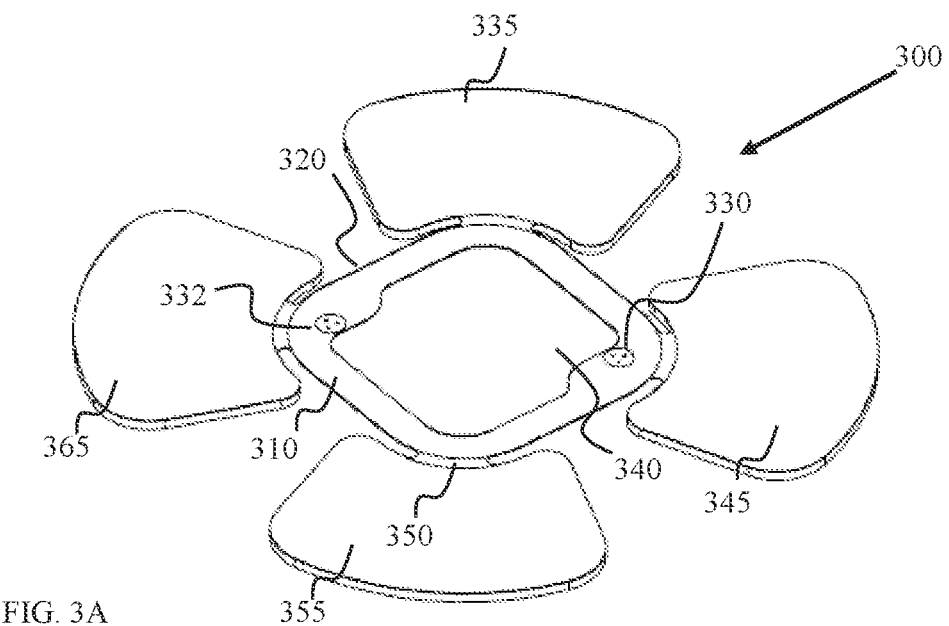
FIG. 3A shows a top view of a sensor module that comprises the multiple light-weight members, according to exemplary embodiments of the subject matter.

FIG. 3A shows a top view of a sensor module that comprises the multiple light-weight members, according to exemplary embodiments of the subject matter. The sensor module 300 comprises one or more electrodes (not shown) located on a bottom surface of the one or more light weight members. For example, one electrode is located at the bottom of each light-weight member. The multiple light-weight members 335, 345, 355, 365 are all connected to a rigid frame 310 that surrounds a void 340. The void 340 is configured to accommodate the bottom surface 260 of the electrical circuit, while the secondary surface 270 resides on top of the rigid frame 310. The multiple light-weight members 335, 345, 355, 365 may be folded relative to the rigid frame 310 using an elastic connector configured to physically secure the multiple light-weight members 335, 345, 355, 365 to the rigid frame. For example, the connector 350 secures the light-weight member 355 to the rigid frame 310. It should be noted that the rigid frame 310 is not fully surrounded by the connectors. For example, lateral void 320 is provided between light-weight members 335 and 365. The void is configured to accommodate the holders of the connecting member.

The rigid frame 310 comprises one or more conductive areas, such as conductive areas 330 and 332. The conductive areas 330 and 332 have a first side located on a frame top surface of the rigid frame 310 and a second side located on the frame bottom surface of the rigid frame 310. The second side located on the bottom surface of the rigid frame 310 is configured to be connected to the conductive members that pass electrical information from the electrodes. The first side of the conductive areas is configured to be secured to the one or more connectors 245, 250, that are connected to the electrical circuit. Thus, the conductive areas 330 and 332 are configured to pass the electrical information from the conductive members to the one or more connectors 245, 250 of the electrical circuit. Electrical information is passed from the first side of the conductive areas 330 and 332 to the second side using one or more apertures configured to contain a conductive fluid, for example conductive ink. The conductive ink may comprise ink mixed with silver, or any other metal. Other conductive fluids may be selected by a person skilled in the art. The one or more apertures enabling passage of the conductive fluid may be in the width of 0.05-0.4 millimeters, throughout the entire depth of the rigid frame 310.

Figure 3B:
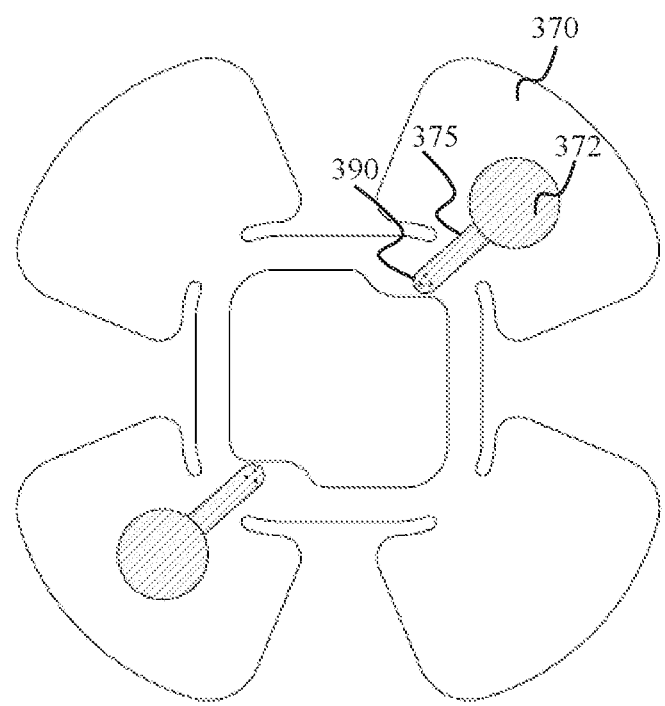
FIG. 3B shows a bottom view of a sensor module that comprises the multiple light-weight members and the electrode, according to exemplary embodiments of the subject matter.

FIG. 3B shows a bottom view of a sensor module that comprises the multiple light-weight members and the electrode, according to exemplary embodiments of the subject matter. The light weight member 370 may be made of fabric, paper, polyethylene or any other light weight and collapsible material. Some examples to materials that can be used to manufacture the light-weight member 370 include thermoplastic elastomers, thermostatic elastomers, polyethylene sheets, polyester sheets, nonwoven fabric, PVC sheets, silicon sheets, wooden logs, paper sheets, LDPE, kapton sheets, sheets made of organic non-conductive materials, sheets for in-mold technology and a combination thereof. The light-weight member 370 have one or more pores enabling passage of the conductive material from the first layer to the second layer. An electrode 372 is attached to the bottom surface of the light-weight member 370. A conductive member 375 is connected to the electrode 372. The conductive member 375 is not in physical contact with the patient's skin. The conductive member 375 is connected to the bottom side 390 of the conductive area. The bottom side 390 comprises multiple apertures enabling passage of the conductive fluid as elaborated above.

Figure 3C:
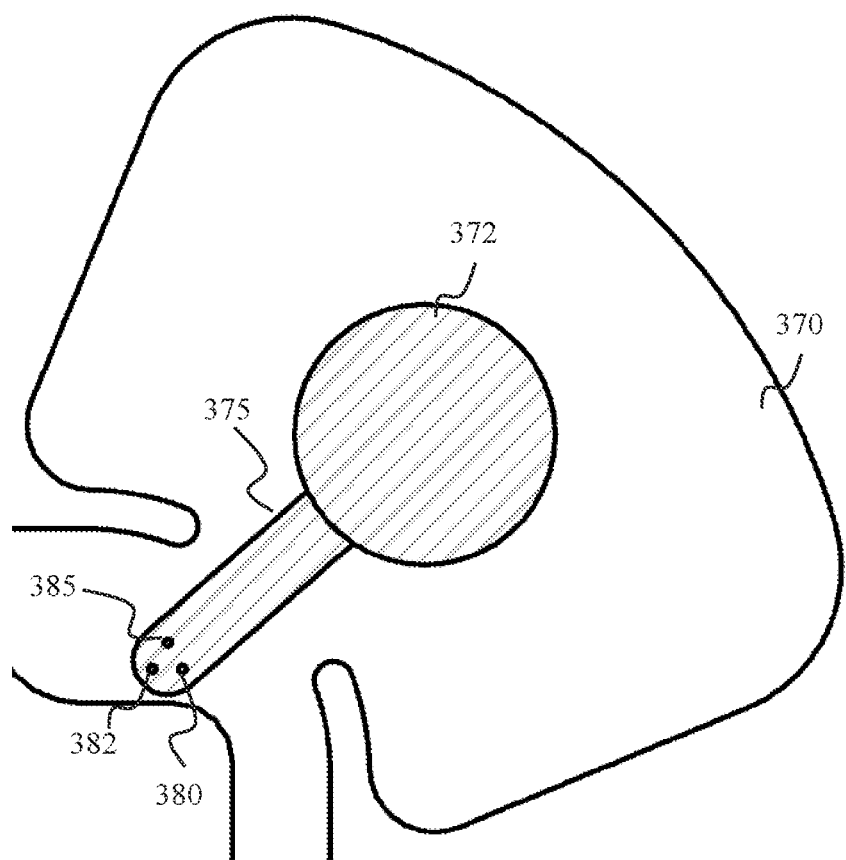
FIG. 3C shows a zoom-in of the conductive area, according to exemplary embodiments of the subject matter.

FIG. 3C shows a zoom-in of the conductive area, according to exemplary embodiments of the subject matter. FIG. 3C shows three apertures 380, 382 and 385, that extend from the bottom surface of the conductive area to the top surface of the conductive area.

Figure 4:
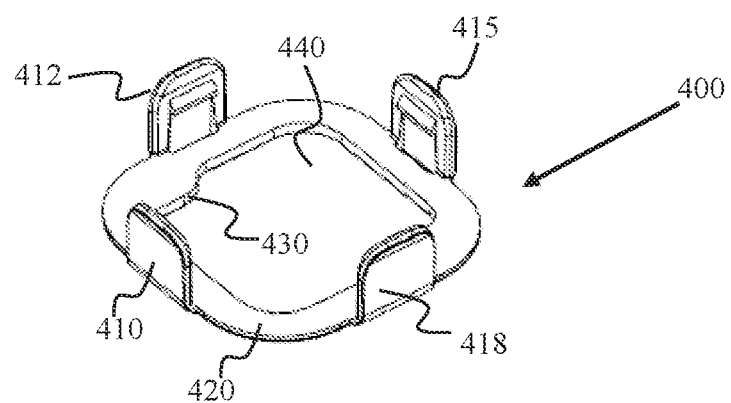
FIG. 4 shows a connecting member comprises multiple holders, according to exemplary embodiments of the subject matter.

FIG. 4 shows a connecting member comprises multiple holders, according to exemplary embodiments of the subject matter. The connecting member 400 is configured to connect the electrical circuit to the light-weight members and secure the housing of the electrical circuit in place. The connecting member 400 comprises a connecting plate 420 configured to be secured to a bottom surface of the rigid frame 310 of the sensor module 300. The connecting member 400 is secured to the sensor module 300 from the bottom direction of the sensor module 300, while the housing of the electrical circuit is secured to the sensor module 300 from the upward direction of the sensor module 300. The upward direction may be defined as the side from which the electrodes are not seen. In some exemplary cases, the connecting plate 420 has a connecting void 440 therein. The connecting void 440 may have substantially the same size and shape as the void 340 of the sensor module 300. The connecting void 440 may have a depth defined by the inner sidewalls 430 of the connecting plate 420. The connecting void 440 may have a higher depth than the depth of the void 340 of the sensor module 300. The connecting void 440 and the void 340 are configured to accommodate the bottom section of the housing of the electrical circuit, defined by the bottom surface 260.

The connecting member 400 also comprises a plurality of holders 410, 412, 415 and 418, configured to secure the housing of the electrical circuit to the rigid frame of the sensor module 300. The plurality of holders 410, 412, 415 may be movable, for example move away from the center of the connecting void 440 when the housing is secured to the sensor module 300, or when the housing is removed therefrom. The plurality of holders 410, 412, 415 may be made of plastics or metal, and may comprise an elastic section, such as a spring, which is tensed when the holders move away from the connecting void 440. Said elastic section pushes the plurality of holders 410, 412, 415 back towards the center of the connecting void 440, thus securing the housing of the electrical circuit in place. In some exemplary cases, the plurality of holders 410, 412, 415 move back into position only when there is electrical conductivity between the electrical circuit and the conductive element that carries the electrical information detected by the electrodes.

Figure 5:
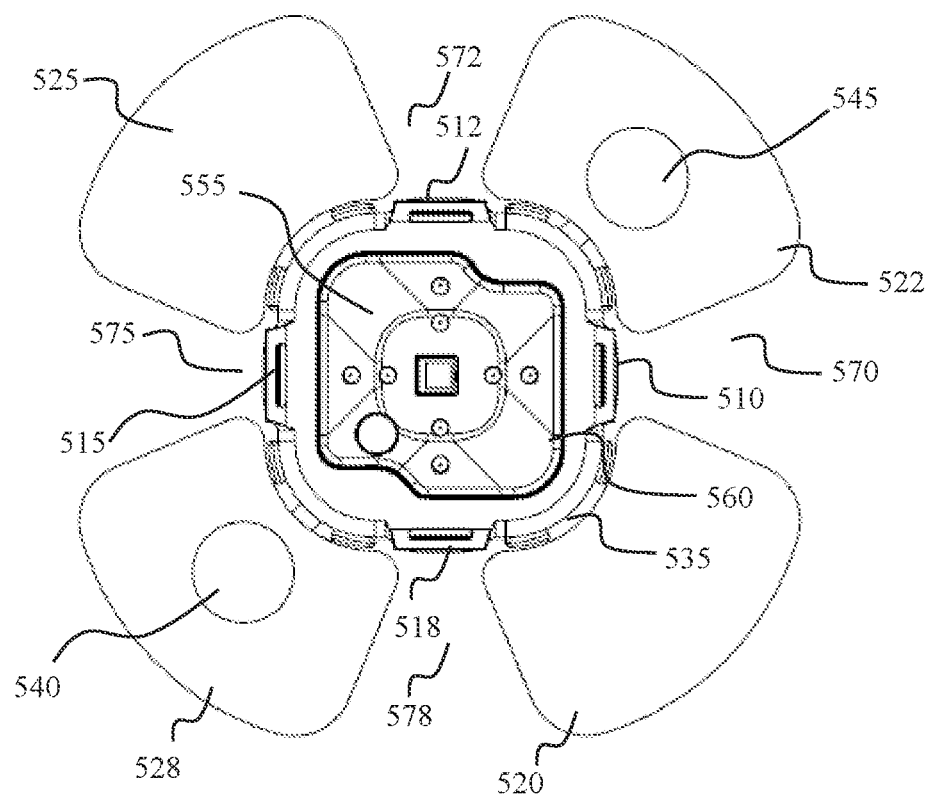
FIG. 5 shows a bottom view of the wearable apparatus when assembled, according to exemplary embodiments of the subject matter.

FIG. 5 shows a bottom view of the wearable apparatus when assembled, according to exemplary embodiments of the subject matter. The wearable apparatus comprises the electrical circuit embodied in a housing secured to the sensor module using a connecting member. FIG. 5 shows a bottom surface 555 of the housing. The bottom surface 555 is configured to be inserted into the connecting void of the connecting member as shown above. The connecting void is defined by frame 560, included in at least the sensor module. The wearable apparatus comprises multiple light-weight members 520, 522, 525 and 528. At least some of the light-weight members 520, 522, 525 and 528 are attached to an electrode in the bottom surface thereof, for example using biocompatible adhesive material, stitching, hooks and loops and the like. For example, light-weight member 528 is attached to electrode 540 and light-weight member 522 is attached to electrode 545. The light-weight members leave lateral voids in the circumference of the frame from which the light weight members extend away from the frame's void. The lateral voids are consumed by a plurality of holders 510, 512, 515 and 518 configured to secure the housing in place. For example, lateral void 570 is formed between light-weight member 522 and light-weight member 520, facilitating passage for holder 510. Similarly, lateral void 572 is formed between light-weight member 522 and light-weight member 525, facilitating passage for holder 512, lateral void 575 is formed between light-weight member 525 and light-weight member 528, facilitating passage for holder 515 and lateral void 578 is formed between light-weight member 528 and light-weight member 520, facilitating passage for holder 518. The light weight members comprise a proximal side which is narrower than the distal side. For example, proximal side 535 of the light-weight member 520.

FIGS. 6A-6B show a top view and a bottom view of the sensor module and the connecting module disassembled, according to exemplary embodiments of the subject matter. The top view shown in FIG. 6A discloses the four light-weight members, such as member 620, connected to the rigid frame 625. The rigid frame 625 comprises conductive areas 640 and 645, configured to be electrically coupled to the conductive elements 650, 655. The conductive elements 650, 655 are attached to the bottom surface of the light-weight members, in a manner that the patient is not in physical contact with the conductive elements 650, 655 when the wearable apparatus is placed on the patient's skin. The electrical information is collected by the electrodes 622, 623, transferred via the conductive elements 650, 655 towards the conductive areas 640 and 645, and to the electrical circuit that processes the electrical information or passes the electrical information to a device that processes the electrical information. The conductive elements 650, 655 are in proximity to the bottom surface of the rigid frame 660. The connecting frame of the connecting member 610 secures the conductive elements 650, 655 between the connecting frame and the rigid frame 660. The light-weight members have a distal side 611 of light weight member 613, and proximal side 612, located closer to the rigid frame 625. The proximal side 612 of the light weight member 613 is narrower than the distal side 611, leaving lateral voids such as 641, 642 that are consumed by the holders, such as holder 615 of the connecting member 610.

Figure 7A:
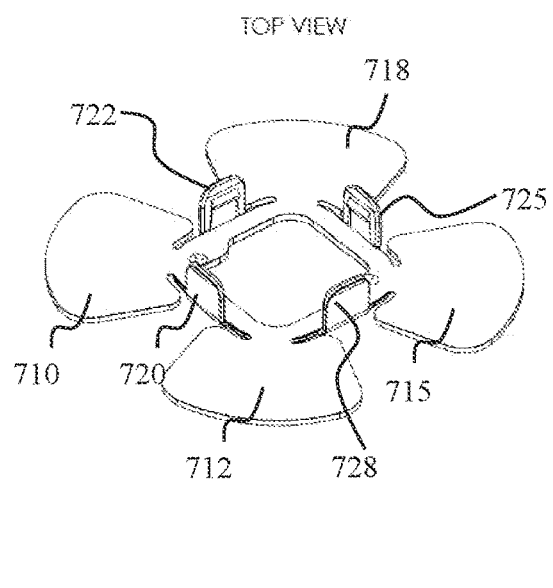
FIGS. 7A-7B show a top view and a bottom view of the sensor module and the connecting module assembled, according to exemplary embodiments of the subject matter; and, FIG. 8 shows a method for assembling a wearable device, according to exemplary embodiments of the subject matter.
Figure 7B:
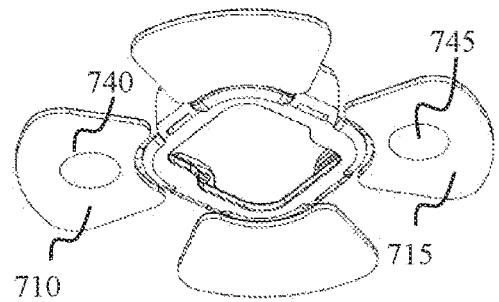

FIGS. 7A-7B show a top view and a bottom view of the sensor module and the connecting module assembled, according to exemplary embodiments of the subject matter. FIG. 7A shows a plurality of light-weight members 710, 712, 715 and 718, having therein the conductive members. The sensor module is attached to the connecting member having a plurality of holders 720, 722, 725 and 728. FIG. 7B shows two electrodes 740, 745 attached to the bottom surface of the light-weight members 710 and 715, respectively.

FIG. 8 shows a method for assembling a wearable device, according to exemplary embodiments of the subject matter. Step 810 discloses obtaining a sensor module, an electrical circuit embodied in a housing and a connecting member. The sensor module comprises one or more electrodes configured to collect electrical information from a patient's skin and pass the electrical information via a conductive element attached to the bottom surface of the light-weight member. The connecting member comprises a void configured to accommodate the bottom section of the housing of the electrical circuit and holders configured to secure the housing to the sensor module.

Step 820 discloses securing the connecting member at a bottom side of the sensor module, thus securing the conductive elements. The conductive elements are secured between the frames of the sensor module and the connecting member, and pass electrical information via the conductive areas of the frame of the sensor module. The connecting member may be secured to the sensor module using mechanical clips. In some other cases, the connecting member secures only the housing of the electrical circuit, which electrically couples to the sensor module. Thus, the coupling of the housing and the sensor module form the connection between the connecting member and the sensor module.

Step 830 discloses mounting the housing from the top section of the sensor module, secured by the holders of the connecting member. The holders are maneuvered away from the center of the void when placing the housing thereon. Then, the elastic member of the holders pushes the holders on the lateral surface of the housing.

Step 840 discloses verifying electrical coupling between the conductivity members and the electrical circuit inside the housing. Such verifying may be performed by receiving an indication from the electrical circuit that electrical information is provided from the electrodes in a sufficient manner. The sufficient manner may be defined by predefined rules stored in the memory unit of the electrical circuit, for example receiving signals having properties in a predefined range.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

What is claimed is:

1. A wearable device for monitoring medical properties of a patient, comprising:
a rigid frame;
multiple members extending from the rigid frame and configured to be secured to skin of the patient;
a housing having an electrical circuit, said housing configured to be secured to the rigid frame and having a bottom surface that protrudes from a secondary surface, wherein the rigid frame is shaped to define a central hole from an upper-most surface of the rigid frame through to a bottom-most surface of the rigid frame, the central hole sized and shaped such that:
(a) the bottom surface of the housing is slidable through the central hole of the rigid frame, and
(b) when the housing is secured to the rigid frame and the multiple members are secured to the patient's skin, the secondary surface from which the bottom surface protrudes is disposed in contact with the rigid frame such that the rigid frame is disposed between the secondary surface and the patient's skin; and
an electrode located on a bottom surface of one of the multiple members, wherein the electrode is configured to collect electrical information from the patient's skin, wherein:
(a) the rigid frame comprises a conductive passageway between (i) the electrode and (ii) a top side of the rigid frame, the conductive passageway configured to conduct the electrical information that is collected from the patient's skin from a bottom side of the rigid frame through to the top side of the rigid frame, and
(b) the housing further comprises a connector located on the secondary surface of the housing, said connector configured to electrically contact the conductive passageway of the rigid frame when the housing is secured to the rigid frame and thereby collect the electrical information that is collected from the patient's skin by the electrode.

2. The wearable device of claim 1, wherein the rigid frame is of a rectangular shape, and wherein the device comprises four members coupled to corners of the rigid frame.

3. The wearable device of claim 1, wherein the electrical circuit is configured to analyze the electrical information collected by the one or more electrodes.

4. The wearable device of claim 1, further comprising a plurality of holders extending from the rigid frame and securable to a lateral surface or a top surface of the housing wherein the plurality of holders comprises an elastic section.

5. The wearable device of claim 1, wherein each one of the members comprises a distal side and a proximal side, said proximal side closer to the rigid frame than the distal side and narrower than the distal side.

6. The wearable device of claim 1, wherein the rigid frame is of a rectangular shape having rounded corners, and wherein the device comprises four members coupled to corners of the rigid frame.

7. The wearable device of claim 6, further comprising a second electrode, located on a bottom surface of a second one of the multiple members.

8. The wearable device of claim 6, wherein each of the members has a rounded shape, the rounded shape having a distal section and a proximal section, the distal section farther from the rigid frame than the proximal section and wider than the proximal section.

9. The wearable device of claim 1, wherein a top surface of the housing comprises an activation button.

10. The wearable device of claim 1, wherein:
the rigid frame is of a rectangular shape having rounded corners, and the device comprises four members, each member coupled to a respective corner of the rigid frame, the device further comprises a second electrode, located on a bottom surface of a second one of the multiple members;

the device further comprises four holders extending from the rigid frame and securable to a lateral surface or a top surface of the housing, each of the four holders extending from a respective side of the rectangular rigid frame;

each of the members has a rounded shape, the rounded shape having a distal section and a proximal section, the distal section farther from the rigid frame than the proximal section and wider than the proximal section; and a top surface of the housing comprises an activation button.

* * * * *